(12) United States Patent
McKennon et al.

(10) Patent No.: US 8,329,853 B2
(45) Date of Patent: Dec. 11, 2012

(54) PROCESS FOR THE PREPARATION OF POLY-α-GLUTAMIC ACID AND DERIVATIVES THEREOF

(75) Inventors: Marc McKennon, Seattle, WA (US); Giovanni Da Re, Milan (IT); Luca Feliciotti, Sesto San Giovanni (IT); Marco Artico, Parabiago (IT); Gianluca Pardi, Ripafratta (IT); Mario Grugni, Novate (IT)

(73) Assignee: Cell Therapeutics, Inc., Seattle, WA (US)

( * ) Notice: Subject to any disclaimer, the term of this patent is extended or adjusted under 35 U.S.C. 154(b) by 0 days.

(21) Appl. No.: 12/965,510

(22) Filed: Dec. 10, 2010

(65) Prior Publication Data
US 2011/0196123 A1    Aug. 11, 2011

Related U.S. Application Data

(63) Continuation of application No. 11/818,056, filed on Jun. 12, 2007, now abandoned.

(60) Provisional application No. 60/813,787, filed on Jun. 15, 2006.

(30) Foreign Application Priority Data

Jun. 15, 2006   (EP) ..................................... 06012351

(51) Int. Cl.
*C08G 69/10*   (2006.01)
(52) U.S. Cl. ....................................... 528/328; 562/555
(58) Field of Classification Search .................. 528/328; 562/555
See application file for complete search history.

(56) References Cited

U.S. PATENT DOCUMENTS

| | | | |
|---|---|---|---|
| 2,629,716 A * | 2/1953 | Morgan | 536/66 |
| 3,635,909 A | 1/1972 | Fujimoto et al. | 260/78 A |
| 3,819,588 A * | 6/1974 | Fujimoto et al. | 525/420 |
| 4,666,886 A * | 5/1987 | Baschang et al. | 514/2.4 |
| 6,590,061 B1 | 7/2003 | Rypacek et al. | 528/288 |
| 7,317,070 B1 * | 1/2008 | Ponnusamy | 528/328 |

FOREIGN PATENT DOCUMENTS

| | | |
|---|---|---|
| EP | 932399 B1 | 1/2006 |
| WO | WO 97/33552 | 9/1997 |
| WO | WO 2007/144140 | 12/2007 |

OTHER PUBLICATIONS

Carey et al. "Functional Group Interconversion by Nucleophilic Substituion," *Adv. Organ. Chem.* 2$^{nd}$ *ed., Chapter 3*:pp. 120-121, 1983.
Gallot et al., "Synthesis and Structural Study by X-Ray Diffraction of Lyotropic Block Lipopeptidic Polymers with Polylysine and Poly(glutamic acid) Peptidic Chains,"*Mol. Cryst. Liq. Cryst.* 153:347-356, 1987.
Lakhanpal, M.L. et al., "Thermodynamic Properties of Partially Miscible Systems: Part I—Binary Systems of Formic Acid with Benzene, Toluene & *p*-Xylene," *Indian Journal of Chemistry* 13(12): 1309-1313, Dec. 1975.
Li, C., "Poly(L-glutamic acid)—anticancer Drug Conjugates," *Advanced Drug Delivery Reviews* 54: 695-713, 2002.
Singer, J.W. et al., "Water-soluble poly-(L-glutamic acid)—Glycamptothecin Conjugated Enhance Camptothecin Stability and Efficacy in vivo," *Journal of Controlled Release* 74: 243-247, 2001.

* cited by examiner

*Primary Examiner* — Satya Sastri
(74) *Attorney, Agent, or Firm* — Seed IP Law Group PLLC

(57) ABSTRACT

The invention relates to an improved process for the preparation of poly-α-glutamic acids which comprises the polymerization of tertiary γ-esters of α-glutamic acid N-carboxy anhydride with appropriate solvents and initiators, followed by acid hydrolysis of the resulting poly-α-glutamic acid-γ-ester. The process is particularly advantageous in that it allows one to carefully control the molecular weight of the resulting poly-α-glutamic acid. The invention also relates to poly-α-glutamic acids capped at the amino terminus with carboxylic acids or amino acids and to a process for the preparation thereof.

30 Claims, No Drawings

PROCESS FOR THE PREPARATION OF POLY-α-GLUTAMIC ACID AND DERIVATIVES THEREOF

CROSS-REFERENCE TO RELATED APPLICATIONS

This application is a continuation of U.S. patent application Ser. No. 11/818,056 filed Jun. 12, 2007, now pending; which application claims the benefit under 35 U.S.C. §119(e) of U.S. Provisional Patent Application No. 60/813,787 filed Jun. 15, 2006 and priority to European Patent Application No. 06012351.0 filed Jun. 15, 2006; which applications are incorporated by reference herein in their entirety.

BACKGROUND

1. Technical Field

The present invention relates to a process for the preparation of poly-α-glutamic acid and derivatives thereof, and compounds therefrom.

2. Description of the Related Art

Poly-α-glutamic acid of formula (I)

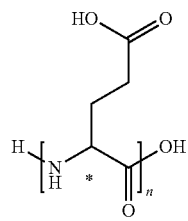

is currently used as drug delivery system, for example for the preparation of conjugates with a wide variety of drugs containing a primary or secondary amino group as well as primary, secondary or tertiary hydroxy groups. The conjugation can occur directly or through a suitable linker, for example an amino acid or a hydroxyacid. See, for example, EP0932399, Advanced Drug Delivery Reviews, Volume 54, Issue 5, 2002, Pages 695-713 and Journal of Controlled Release, Volume 74, Issues 1-3, 2001, Pages 243-247.

Poly-α-glutamic acid can be synthesized by polymerization of suitably protected glutamic acid. U.S. Pat. No. 3,635,909 discloses, inter alia, the polymerization of D-glutamic acid-γ-(tert-butyl)ester N-carboxy anhydride in a 1,2-dichloroethane/1,4-dioxane mixture using sodium 4-methyl-2-pyrrolidone as initiator.

BRIEF SUMMARY

Briefly stated, compounds and processes for the preparation of poly-α-glutamic acid and derivatives thereof are provided.

In an embodiment, the present invention provides a process for the preparation of poly-α-glutamic acid of formula (I)

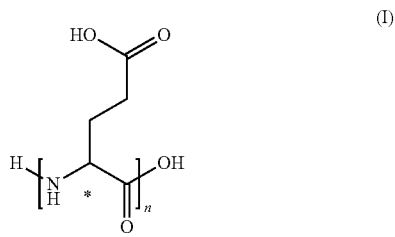

wherein the symbol * indicates a chiral center and n is between 60 and 310, so that the poly-α-glutamic acid has a molecular weight ranging from 8,000 to 40,000 Da the process comprising the steps of:

a) polymerization of a tertiary γ-ester of α-glutamic acid N-carboxy anhydride of formula (II)

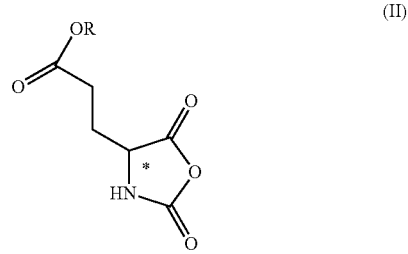

wherein the symbol * is as defined above and R is selected from t-butyl, 1,1-dimethylpropyl and 1,1-dimethylbutyl in water or in an organic solvent selected from: tetrahydrofuran, 1,4-dioxane, dimethylformamide, 1,4-dioxane/DMF and 1,4-dioxane/tetrahydrofuran mixture with an initiator selected from potassium tert-butoxide, sodium methoxide, diisopropylethylamine, 1,8-diazabicyclo[5,4,0]undec-7-ene, dimethylaminopyridine and L-glutamic acid-γ-tert-butylester, to give a compound of formula (III)

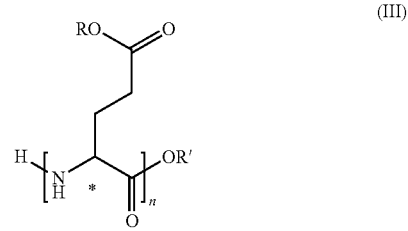

wherein * and R are as defined above and R' is hydrogen when the initiator is selected from diisopropylethylamine, 1,8-diazabicyclo[5,4,0]undec-7-ene, 4-dimethylaminopyridine, glutamic acid dimethyl ester and glutamic acid-γ-tert-butyl ester or R' is a t-butyl or methyl group when the initiator is potassium tert-butoxide and sodium methoxide respectively; and followed by b) acid hydrolysis of the γ- and α-ester groups to give a compound of formula (I).

In an embodiment, the present invention provides a process for the preparation of a poly-α-glutamic acid derivative of formula (IV)

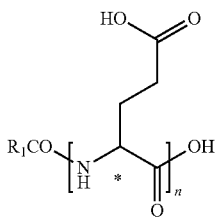

(IV)

wherein the symbol * indicates a chiral center and n is an integer comprised between 60 and 310 and $R_1CO-$ is selected from:
- $(C_1-C_{10})$alkylcarbonyl;
- $(C_4-C_8)$cycloalkylcarbonyl;
- $(C_2-C_6)$carboxyalkylcarbonyl;
- $(C_6-C_{10})$arylcarbonyl;
- $(C_6-C_{10})$aryl$(C_1-C_{10})$alkylcarbonyl;
- $(C_1-C_{10})$alkyl$(C_6-C_{10})$arylcarbonyl;
- $(C_5-C_{10})$heteroarylcarbonyl and $(C_5-C_{10})$heteroaryl$(C_1-C_{10})$alkylcarbonyl wherein the heteroaromatic ring contains one or more nitrogen, oxygen or sulphur atoms; and
- D- or L-amino acid and non-natural amino acid residues;

the process comprising the steps of:

a) polymerization of a tertiary γ-ester of an α-glutamic acid N-carboxy anhydride of formula (II)

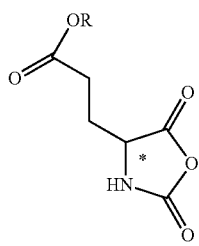

(II)

wherein * is as defined above and R is selected from t-butyl, 1,1-dimethylpropyl and 1,1-dimethylbutyl
in water or in an organic solvent selected from: tetrahydrofuran, 1,4-dioxane, dimethylformamide, 1,4-dioxane/DMF and 1,4-dioxane/tetrahydrofuran mixtures with an initiator selected from potassium tert-butoxide, sodium methoxide, diisopropylethylamine, 1,8-diazabicyclo[5,4,0]undec-7-ene, dimethylaminopyridine and L-glutamic acid-γ-tert-butylester, to give a compound of formula (III);

b) reaction of a compound of formula (III)

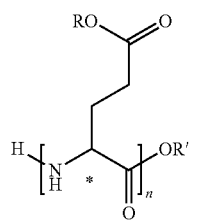

(III)

obtained according to step a) above with a carboxylic acid $R_1COOH$, or an acyl chloride $R^1COCl$ or an anhydride $(R_1CO)_2O$ wherein $R_1$ is as defined above, in the presence of a dehydrating agent to give a compound of formula (V)

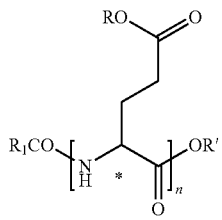

(V)

and c) the hydrolysis of the compound of formula (V) to give a compound of formula (IV).

In an embodiment, the present invention provides a poly-α-glutamic acid derivative of formula (IV)

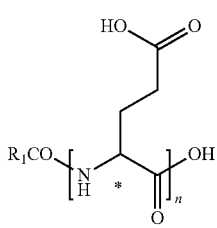

(IV)

wherein the symbol * indicates a chiral center and n is an integer comprised between 60 and 310 and $R_1CO-$ is selected from:
- $(C_1-C_{10})$alkylcarbonyl;
- $(C_4-C_8)$cycloalkylcarbonyl;
- $(C_6-C_{10})$arylcarbonyl;
- $(C_6-C_{10})$aryl$(C_1-C_{10})$alkylcarbonyl;
- $(C_1-C_{10})$alkyl$(C_6-C_{10})$arylcarbonyl;
- $(C_5-C_{10})$heteroarylcarbonyl and $(C_5-C_{10})$heteroaryl$(C_1-C_{10})$alkylcarbonyl wherein the heteroaromatic ring contains one or more nitrogen, oxygen or sulphur atoms; and
- D- or L-amino acid and non-natural amino acid residues as well as their salts with inorganic acids or bases.

In an embodiment, the present invention provides a poly-α-glutamic acid derivative of formula (V)

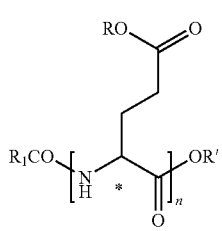

(V)

wherein the symbol * indicates a chiral center and n is an integer comprised between 60 and 310, R is selected from t-butyl, 1,1-dimethylpropyl and 1,1-dimethylbutyl, R' is hydrogen or a t-butyl or methyl group and $R_1CO$ is selected from:
- $(C_1-C_{10})$alkylcarbonyl;
- $(C_4-C_8)$cycloalkylcarbonyl;
- $(C_6-C_{10})$arylcarbonyl;
- $(C_6-C_{10})$aryl$(C_1-C_{10})$alkylcarbonyl;
- $(C_1-C_{10})$alkyl$(C_6-C_{10})$arylcarbonyl;

($C_5$-$C_{10}$)heteroarylcarbonyl and ($C_5$-$C_{10}$)heteroaryl($C_1$-$C_{10}$)alkylcarbonyl wherein the heteroaromatic ring contains one or more nitrogen, oxygen or sulphur atoms; and D- or L-amino acid and non-natural amino acid residues.

These and other aspects of the present invention will become apparent upon reference to the following detailed description.

DETAILED DESCRIPTION

The present disclosure shows that appropriate choice of the solvent and of the initiator allows the control of the molecular weight of poly-α-glutamic acid prepared from tertiary γ-esters of α-glutamic acid N-carboxy anhydride. Accordingly, in one aspect the invention relates to a process for the preparation of poly-α-glutamic acid of formula (I)

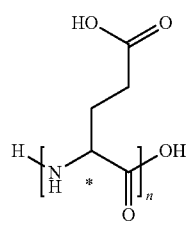

(I)

wherein n is an integer comprised between 60 and 310, so that the poly-α-glutamic acid has a molecular weight ranging from 8,000 to 40,000 Da, preferably from 10,000 to 35,000 Da, more preferably from 13,000 to 16,000 Da, and with a polydispersity index usually ≦2, preferably ≦1.5, said process comprising the steps of:

a. polymerization of a tertiary γ-ester of α-glutamic acid N-carboxy anhydride of formula (II)

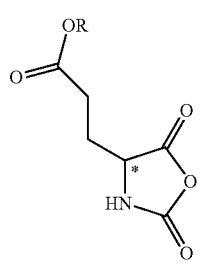

(II)

wherein R is selected from t-butyl, 1,1-dimethylpropyl- and 1,1-dimethylbutyl- and is preferably a t-butyl group either in water or in an organic solvent selected from tetrahydrofuran (THF), 1,4-dioxane, dimethylformamide (DMF), 1,4-dioxane/DMF and 1,4-dioxane/tetrahydrofuran mixtures with an initiator selected from potassium tert-butoxide (t-BuOK), sodium methoxide (MeONa), diisopropylethylamine, 1,8-diazabicyclo[5,4,0]undec-7-ene (DBU), 4-dimethylaminopyridine (DMAP), glutamic acid dimethyl ester, and glutamic acid-γ-tert-butyl ester, to give a compound of formula (III)

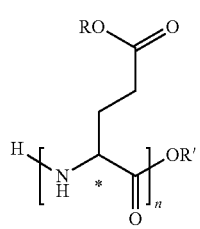

(III)

wherein n and R are as defined above and R' is hydrogen when the initiator is selected from diisopropylethylamine, 1,8-diazabicyclo[5,4,0]undec-7-ene (DBU), 4-dimethylaminopyridine (DMAP), glutamic acid dimethyl ester and glutamic acid-γ-tert-butyl ester or R' is a t-butyl or methyl group when the initiator is t-BuOK and MeONa respectively; and followed by b. acid hydrolysis of the γ- and α-ester groups to give a compound of formula (I).

Throughout the specification, the symbol * indicates a chiral center and the term glutamic acid comprises both the L- and D-form, either as pure isomers or as racemic mixture.

Step a) is usually carried out at a temperature ranging from 10 to 50° C., with a concentration of the γ-ester of α-glutamic acid N-carboxy anhydride ranging from 0.1 to 0.3 M. According to a preferred embodiment, the process is carried out using 1,4-dioxane as the solvent and DBU as the initiator.

The molar ratio of γ-ester of α-glutamic acid N-carboxy anhydride to initiator usually ranges from 2 to 25; the molar ratio of γ-ester of α-glutamic acid N-carboxy anhydride to α-glutamic acid γ-ester is 100.

Step b) can be carried out using any reagent conventionally used for the removal of tert-butyl esters, as exemplified by those described in "Protective groups in organic synthesis" Third edition, Theodora W. Greene and Peter G. M. Wuts, a Wiley-Interscience publication—John Wiley & Sons, Inc, page 406-408 and references therein. Preferred conditions include trifluoroacetic acid (TFA), formic acid and water/formic acid mixtures at a temperature ranging from 20 to 60° C.; TFA is used in amount of 100 v/w, while formic acid and water/formic acid mixtures are used in amounts ranging from 20 to 50 v/w.

The process of the invention is suitable for preparing both the D and L form of poly-α-glutamic acids, in particular the L form. Moreover, the poly-α-glutamic acids prepared according to the invention can be easily converted into their acidic or basic salts by reaction with inorganic acids, such as hydrochloric acid, hydrobromic acid, sulphuric acid, nitric acid, perchloric acid or with inorganic bases such as alkaline or alkaline-earth metal hydroxides and ammonium hydroxide.

The process of the invention provides poly-α-glutamic acid with a weight average molecular weight ($M_w$) determined by Gel Permeation Chromatography combined with Multi Angle Laser Light Scattering detection, ranging within the values defined above, preferably between 13,000 and 16,000 Da and with a polydispersity index ≦1.5. This is particularly advantageous, since the procedures disclosed in the literature, through different γ-protecting groups (such as benzyl, methyl or ethyl; see Polymer monographs, Volume 9: H. Block, Poly(γ-benzyl-L-glutamate) and other glutamic acid containing polymers. Edited by B. Huglin, University of Salford), afford materials of uncontrolled and very high molecular weight, which often require chromatographic separation to isolate poly-α-glutamic acids having a desired molecular weight range.

Moreover, the process of the invention allows avoidance of spontaneous formation of a pyroglutamic ester at the amino terminus, which usually occurs during polymerization using, for example, γ-benzyl, γ-methyl or γ-ethyl glutamic acid ester N-carboxy anhydride. In fact, currently available poly-α-glutamic acids exhibit either a pyroglutamic terminus, or an amino terminus or a mixture thereof. Suppression of formation of a pyroglutamic terminus is achieved in particular when a compound of formula (II) wherein R is a t-butyl group is used as the starting material. Poly-α-glutamic acids γ-esters with a free amino terminus can thus be reacted either with stoichiometric amounts of pyroglutamic acid or with other suitable acids, so as to achieve 100% conversion into the desired N-capped poly-α-glutamic acid.

Accordingly, in another aspect the present invention provides also a process for the preparation of poly-α-glutamic acid derivatives of formula (IV)

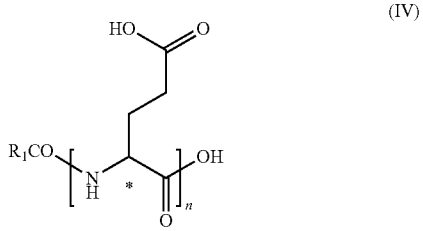
(IV)

wherein n is as defined above and $R_1CO-$ is selected from:
$(C_1-C_{10})$alkylcarbonyl; $(C_4-C_8)$cycloalkylcarbonyl; $(C_2-C_6)$carboxyalkylcarbonyl; $(C_6-C_{10})$arylcarbonyl; $(C_6-C_{10})$aryl$(C_1-C_{10})$alkylcarbonyl; $(C_1-C_{10})$alkyl$(C_6-C_{10})$arylcarbonyl; $(C_5-C_{10})$heteroarylcarbonyl and $(C_5-C_{10})$heteroaryl$(C_1-C_{10})$alkylcarbonyl wherein the heteroaromatic ring contains one or more nitrogen, oxygen or sulphur atoms; D- or L-natural and non-natural amino acid residues said process comprising reacting a compound of formula (III)

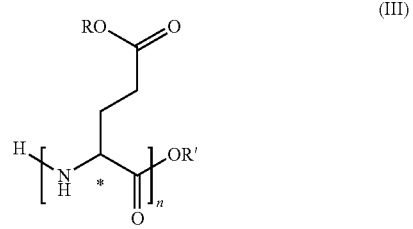
(III)

obtained according to step a) above with a carboxylic acid $R_1COOH$ in the presence of a dehydrating agent, or with an activated carboxylic acid, such as an acyl chloride $R_1COCl$ or an anhydride $(R_1CO)_2O$, wherein $R_1CO-$ is as defined above, to give a compound of formula (V)

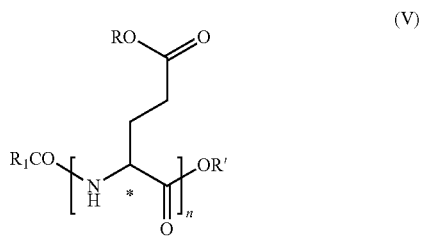
(V)

and hydrolyzing the compound of formula (V) to a compound of formula (IV).

In the compounds of formula (IV) and (V):
examples of $(C_1-C_{10})$alkylcarbonyl are acetyl and butyryl;
examples of $(C_4-C_8)$cycloalkylcarbonyl are cyclopropylcarbonyl, cyclobutanecarbonyl, cyclohexylcarbonyl;
example of $(C_2-C_6)$carboxyalkylcarbonyl is succinyl;
examples of $(C_6-C_{10})$aryl carbonyl are benzoyl, 1-naphthoyl, 2-naphthoyl;
examples of $(C_6-C_{10})$aryl$(C_1-C_{10})$alkylcarbonyl are phenylacetyl and phenylbutyryl;
examples of $(C_1-C_{10})$alkyl$(C_6-C_{10})$arylcarbonyl are o-, m- and p-tolyl;
examples of $(C_5-C_{10})$heteroarylcarbonyl are nicotinoyl, N-methylpyrrole-3-carbonyl, 3-thiophenecarbonyl and 3-quinolinecarbonyl;
example of $(C_5-C_{10})$heteroaryl$(C_1-C_{10})$alkylcarbonyl is 3-pyridyl acetyl;
examples of D- or L-natural amino acid residues are those deriving from glycine, alanine, valine, leucine, isoleucine, serine, threonine, lysine, pyroglutamic acid, phenylalanine, tryptophan, cysteine;
examples of non-natural amino acid residues are those deriving from β-alanine, α,α-dimethylglycine, α-phenylglycine, homophenylalanine, 3-amino-3-(4-methylphenyl)propionic acid, and 2-(1-aminocyclopentyl)acetic acid.

The reaction between compound (III) and the acid $R_1COOH$ is carried out in the presence of a dehydrating agent commonly used in peptide chemistry, like carbodiimides, such as dicyclohexylcarbodiimide and diisopropylcarbodiimide, uronium salts, such as 2-1H-7-azabenzotriazol-1-yl-1,1,3,3-tetramethyl uronium hexafluorophosphate methanaminium (HATU), 2-(1H-benzotriazol-1-yl)-1,1,3,3-N,N,N',N'-tetramethyluronium-hexafluorophosphate (HBTU) and 2-(1H-6-chlorobenzotriazol-1-yl)-1,1,3,3-N,N,N',N'-tetramethyluronium-hexafluorophosphate (HCTU), phosphonium salts, such as benzotriazol-1-yloxytris(pyrrolidino) phosphonium hexafluorophosphate (PyBOP), and the like. When a natural or non-natural amino acid is used as the capping agent, its amino group is preferably protected by a suitable protecting group, preferably the t-butoxycarbonyl protecting group. Subsequent acidic hydrolysis of the N-capped poly-α-glutamic acid-γ-ester as described in step b) above then provides the N-capped poly-α-glutamic acid. If desired, the compounds of formula (IV) can be converted into their acidic or basic salts by reaction with inorganic acids, such as hydrochloric acid, hydrobromic acid, sulphuric acid, nitric acid, perchloric acid or with inorganic bases such as alkaline or alkaline-earth metal hydroxides and ammonium hydroxide.

The compounds of formula (IV) and (V) are disclosed as another aspect of the present invention.

A particularly preferred embodiment is a compound of formula (IV) wherein $R_1CO$ is a D- or L-pyroglutamic acid residue and the content of the N-terminus free amine is lower than 1% w/w, preferably lower than 0.2% w/w.

The process described above for the preparation of a compound of formula (IV) has general applicability, that is to say that, further to a carboxylic acid $R_1COOH$, or an activated carboxylic acid, such as an acyl chloride $R_1COCl$ or an anhydride $(R_1CO)_2O$, any compound able to react with the —NH$_2$ terminus can be used for the reaction with the compound of formula (III). Examples of such compounds are aldehydes, ketones, α,β-unsaturated ketones, sulfonyl chlorides and nitriles, which can be reacted with compound (III) according to methods known to the skilled chemist. According to a further embodiment of the invention either the carboxylic acid, or activated carboxylic acid, or anhydride, or compound able to react with the —NH$_2$ terminus may also bear at least a group, such as a hydroxy, an amino or a thio group, which can be further functionalized with a moiety suitable for modulating the pharmacokinetic properties of poly-α-glutamic acid. Therefore, another aspect of the present invention is also a poly-α-glutamic acid substituted at the —NH₂ terminus with a group which is able to be further functionalized with a moiety suitable for modulating the pharmacokinetic properties of poly-α-glutamic acid.

Embodiments of the invention will be hereinafter illustrated in greater detail in the following examples. The examples are offered by way of illustration and not by way of limitation.

EXAMPLES

Example 1

Step a—Preparation of L-α-Glu-NCA-γ-tBu ester

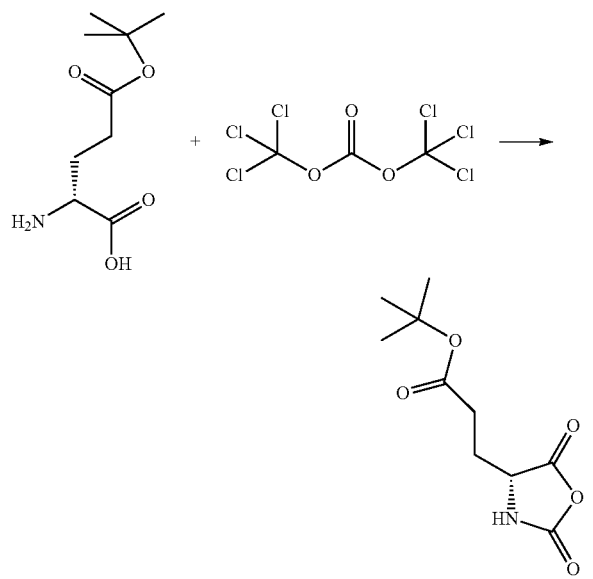

40.17 g of triphosgene (0.135 mol; phosgene/L-Glu-γ-tBu ester 2.74/1) and 862.5 mL of THF were placed under nitrogen into a 1 L jacketed reactor, equipped with mechanical stirrer. The reactor was thermostated at 20° C. and the mixture was stirred until complete dissolution of triphosgene (a few minutes are necessary), thereafter 30 g of L-α-Glu-γ-tBu ester (0.148 mol) were added in a single portion and quite rapidly. The resulting suspension was allowed to react for 2 hours at 20° C. At the beginning exothermicity was observed (≈4° C.), then the solid dissolved as the reaction proceeded: after about 30 min a clear solution was obtained.

At the end of the reaction the solvent was evaporated under reduced pressure, keeping the jacket temperature not higher than 20° C.: the distillation was quite tumultuous. The distillation was continued until a dense and oily residue was obtained, without solids (about 80 mL of residue expected). At the end of the distillation 750 mL of n-heptane were dropped in over about 15 min and the mixture was stirred under nitrogen at 20/23° C. for 1 hour until complete crystallization of the product. Usually, crystallization begins after addition of 150 mL of n-heptane.

The resulting pure white solid was filtered on a buchner funnel and washed with 3×90 mL of n-heptane, then dried in the oven under dynamic vacuum at 20/25° C. for no longer than 20 hours. The solid must be used as soon as possible and must be stored under static vacuum in the presence of silica gel.

Starting from 30 g of L-α-Glu-γ-tBu ester, 23.3 g of L-α-Glu-NCA-γ-tBu ester were obtained (68.8% yield).

Step b—Polymerization of α-L-glutamic acid-γ-(tert-butyl)ester N-carboxy anhydride) (NCA) to poly-α-L-glutamic acid-γ-(tert-butyl)ester

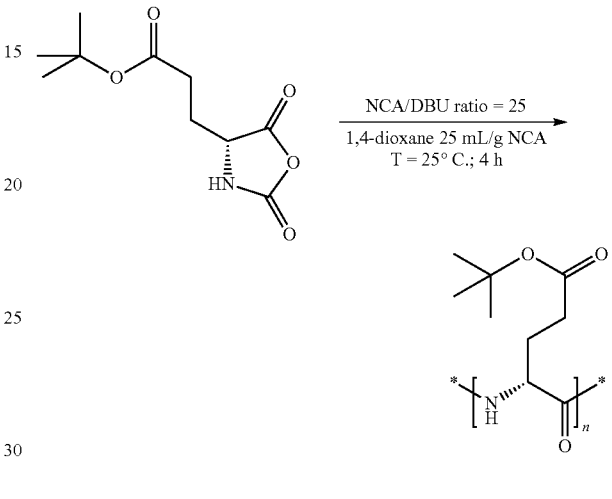

1,8-Diazabiciclo[5.4.0]undec-7-ene free base (DBU; MW 152.24; 585 mg, 3.84 mmol) was dissolved in 1,4-dioxane (5 mL from the total amount) in few minutes.

In a 1 L jacketed glass reactor 1,4-dioxane (550 mL) and α-L-glutamic acid-γ-(tert-butyl)ester N-carboxy anhydride (NCA) (22 g, 96 mmol; NCA/DBU=25) were mixed at 25° C. until dissolution was complete.

The resulting solution was added very quickly with the previously prepared DBU solution. A precipitate instantly appeared and low exothermicity was observed (about 3° C.).

The mixture was stirred for 4 hours, then water (1100 mL) was slowly poured in over 30 to 40 minutes. After a further 30 minutes stirring at 25° C. the precipitated solid was collected by filtration and washed with water (3×50 mL). The recovered white solid was then dried under vacuum at 40° C. to yield 16.4 g of pure material, t-BuPG (92% recovery; $DP_n$=137.2, number average degree of polymerization; $M_n$=25,400 Da, number average molecular weight from $^1$H-NMR).

Step c—Hydrolysis of poly-α-L-glutamic acid-γ-(tert-butyl)ester to poly-α-L-glutamic acid

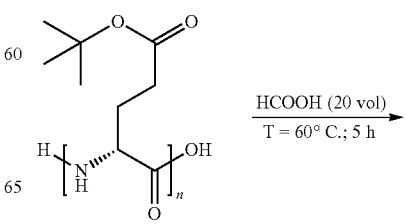

-continued

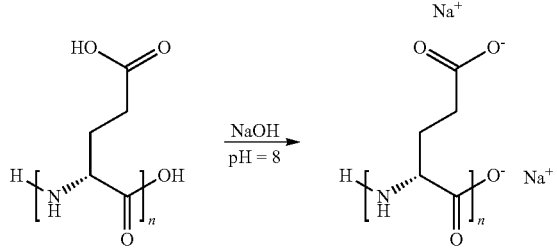

Solid poly-α-L-glutamic acid-γ-(tert-butyl)ester (4 g) was suspended in formic acid 99% (80 mL, 20 volumes) under nitrogen atmosphere in a 100 mL jacketed glass reactor. The mixture was stirred at 60° C. for 5 hours. After about a 30-minute heating the suspension turned into solution, then a solid began to precipitate.

Most of the formic acid was then removed by distillation under reduced pressure (P=15 torr; internal temperature always below 60° C.). The residual formic acid was evaporated off by azeotropic distillation with toluene (2×40 mL; T<40° C.).

The resulting residue was suspended in water (40 mL) and the mixture was cooled to 3-5° C., then 30% w/w NaOH was carefully added to reach pH 8. Once the pH was stable at 23-25° C., the resulting solution was filtered through a 0.22 μm microfilter.

The clear solution was acidified by means of sulphuric acid up to pH 2.5, then the resulting suspension was stirred for 2 hours. The precipitated solid was filtered off and dried under vacuum (30° C. overnight). A white cake was recovered (2.7 g) with a $M_w$=13,900 Da and polydispersity 1.04 (GPC-MALLS).

Example 2

α-L-glutamic acid-γ-(tert-butyl)ester N-carboxy anhydride (3.95 g, 17.2 mmol) was dissolved, under nitrogen stream, in THF (100 mL) to reach a concentration of 0.039 g/mL (0.17 M). The stirring speed was set to 800 rpm.

Then DBU (105 mg, A/I=25) was added by a syringe very quickly and the mixture was stirred for 4 hours at 22-23° C. A slight exotherm was observed soon after addition of the initiator.

Afterwards, the reaction mixture was concentrated to dryness and the residue was rinsed with fresh 1,4-dioxane (100 mL). Two volumes of water were then added to the reaction mixture which was stirred for 30 minutes. The precipitated solid was collected, washed with water and dried under vacuum at 40° C. for at least 12 hours.

2.85 g of poly-α-L-glutamic acid-γ-(tert-butyl)ester (90% recovery) as a white powder with $M_n$=34,100 Da and $DP_n$=184 (by $^1$H-NMR) were obtained.

The resulting poly-α-L-glutamic acid-γ-(tert-butyl)ester was then hydrolyzed in hot 99% HCOOH according to the procedure described in step c of Example 1, furnishing about 1.7 g of poly-α-L-glutamic acid (84% recovery) with $M_w$=25,700 and polydispersity=1.2 according to Gel Permeation Chromathography coupled with Multi Angle Laser Light Scattering analysis.

Example 3

General Procedure for the Polymer Capping Reaction

A typical poly-α-L-glutamic acid-γ-(tert-butyl)ester, obtained according to an experimental procedure herein described (see Example 1 and 2), contains about 1% moles of free amino groups at the N-terminus, as determined by $^1$H-NMR analysis. This percentage was used to calculate the molar equivalents of the suitable acid to add to poly-α-L-glutamic acid-γ-(tert-butyl)ester for its capping reaction.

Poly-α-L-glutamic acid-γ-(tert-butyl)ester was dissolved in THF (20 mL/g) then a catalytic amount of 4-dimethylaminopyridine (DMAP; about 5-10% moles with respect to the added acid) was added. The suitable acid (10 molar equivalents) was added to the previous mixture and diisopropylcarbodiimide (DIPC, 50% molar excess with respect to the acid added) was dropwise added in about 10 min. The solution was stirred for 2 hours.

Two volumes of water were then added and the resulting mixture was stirred for 30 min. The precipitated solid consisting of N-acyl-poly-α-L-glutamic acid-γ-(tert-butyl)ester was collected and then suspended in formic acid (20 volumes). After stirring at 60° C. for 2 h, two volumes of water were added and the resulting mixture was stirred for 30 min. The precipitated solid was removed by filtration, washed with water and dried under vacuum (30° C., overnight) to yield a suitably N-capped poly-α-L-glutamic acid (N-acyl-poly-L-α-glutamic acid).

Example 3A

Poly-α-L-glutamic acid-γ-(tert-butyl)ester (1 g, 5.37 mmol) was dissolved in THF (20 mL) and catalytic DMAP (8 mg, 0.07 mol) was added. Then N—BOC-L-Phenylalanine (180 mg, 0.7 mol) was added to the mixture and immediately after DIPC (160 μL, 1 mmol) was dropwise added. The resulting solution was stirred for about two hours then water (2 volumes) was added and a white precipitate formed immediately. The suspension was stirred for 30 min and filtered, then the white powdered solid was suspended in formic acid (18 mL). The resulting mixture was stirred for 2 h at 60° C. and formic acid was removed by distillation at reduced pressure (P=15 torr) followed by azeotropic distillation with toluene (2×10 mL of toluene) under slight vacuum (Lakhanpal M. L.; Mandal H. G.; Lal G.; Indian J. Chem, 13, 1309 (1975)). The solid residue was dissolved in aqueous NaHCO$_3$ and the resulting solution was ultrafiltered through a 5,000 Da cutoff membrane. The retentate was concentrated to about 30 mL and acidified with sulphuric acid until pH 2-2.5. The precipitated material was stirred for 30 min and recovered by filtration yielding, after drying under vacuum (30° C., overnight), the corresponding N-terminus phenylalanine-capped poly-α-L-glutamic acid, i.e., N-phenylalanyl-poly-α-L-glutamic acid (530 mg, 84% recovery). The $^1$H-NMR was consistent with the proposed structure.

The N-terminal free amine content (clearly detectable at the poly-α-L-glutamic acid-γ-(tert-butyl)ester stage) was no longer detectable by $^1$H-NMR analysis or by analysis following derivatization with o-phthalaldehyde.

$M_w$=13,300 polydispersity=1.16 as determined by GPC-MALLS analysis.

Example 3B

Poly-α-L-glutamic acid-γ-(tert-butyl)ester (1 g, 5.37 mmol) was dissolved in THF (40 mL) and DMAP (42 mg, 0.34 mol) was added. Then L-pyroglutamic acid (44 mg, 0.34 mol) was added to the mixture and immediately after DIPC (106 μL, 0.7 mmol) was dropwise added. The resulting solution was stirred for about two hours then water (2 volumes) was added and a white precipitated formed immediately. The suspension was stirred for 30 min, then filtered and the recovered white powder was suspended in formic acid (18 mL). The resulting mixture was stirred for 2 h at 60° C. and formic acid was removed by distillation at reduced pressure (P=15 torr) followed by azeotropic distillation with toluene (2×10 mL of toluene) under slight vacuum. The solid residue was dissolved in aqueous NaHCO$_3$ and the resulting solution was ultrafiltered through a 5,000 Da cutoff membrane. The retentate was concentrated to about 30 mL and acidified by means of sulphuric acid until pH 2-2.5. The precipitated material was stirred for 30 min and recovered by filtration yielding, after drying under vacuum (30° C., overnight), the corresponding N-terminus pyro-L-glutamic-capped poly-α-L-glutamic acid (400 mg, 64% recovery). The $^1$H-NMR was consistent with the proposed structure and the free amine (clearly detectable at the poly-α-L-glutamic acid-γ-(tert-butyl)ester stage) was no longer detectable by $^1$H-NMR or o-phthalaldehyde analysis.

Example 3C

Naphthalen-2-yl-acetic acid (19.7 mg, 0.106 mmol) and N-methyl morpholine (23.7 mg, 25.7 μL, 0.234 mmol) were dissolved in CH$_2$Cl$_2$ (10 mL) and the mixture was cooled at 0° C.
Chlorotripyrrolidinophosphonium hexafluorophosphate (PyClop, 0.106 mmol, 44.7 mg) was added to the mixture and the resulting solution was stirred for about 1 hour, then poly-α-L-glutamic acid-γ-(tert-butyl)ester was added quickly (n≈100; 1 g, 0.054 mmol) and the reaction was stirred for additional 5 hours after the removal of the cooling bath. The solvent was evaporated under reduced pressure. The crude material was dissolved again in THF (10 mL) and water (2 volumes) was added. The resulting suspension was stirred for 30 min, then it was filtered and the recovered white powder was suspended in formic acid (18 mL). The resulting mixture was stirred for 2 h at 60° C. The mixture was cooled down and formic acid was removed by distillation at reduced pressure (P=15 torr) followed by azeotropic distillation with toluene (2×10 mL each). The solid residue was dissolved in aqueous NaHCO$_3$ and the resulting solution was ultrafiltered through a 5000 Da cutoff membrane. The retentate was concentrated to about 30 mL and acidified by means of sulfuric acid until pH 2-2.5. The precipitated material was stirred for 30 min and recovered by filtration yielding, after drying under vacuum (30° C., overnight), the corresponding N-(Naphthalen-2-yl-acetyl)-poly-α-L-glutamic acid (570 mg, 82% recovery). The $^1$H-NMR was consistent with the proposed structure and the free amine (clearly detectable at the poly-α-L-glutamic acid-γ-(tert-butyl)ester stage) was no longer detectable by $^1$H-NMR or o-phthalaldehyde analysis.

Example 3D

Naphthalen-2-yl-acetic acid (31.7 mg, 0.17 mmol), TEA (3.5 mg, 4.7 μL, 0.034 mmol) and N,N'-disuccinimidyl carbonate (DSC, 43.6 mg 0.17 mmol), were dissolved in a 1:1 mixture of CH$_2$Cl$_2$/CH$_3$CN (2 mL) and the resulting mixture was stirred at room temperature for 2 hours. The mixture was dropwise added to a poly-α-L-glutamic acid-γ-(tert-butyl)ester (n≈100; 1 g, 0.054 mmol) solution in CH$_2$Cl$_2$ (10 mL) and the resulting solution was stirred overnight. The solvent was then removed under reduced pressure and the crude material was processed in the same way as described in the Example 3C.
The recovered solid, after drying under vacuum (30° C., overnight), furnished the corresponding N-(Naphthalen-2-yl-acetyl)-poly-α-L-glutamic acid (612 mg, 88% recovery). The $^1$H-NMR was consistent with the proposed structure and the free amine (clearly detectable at the poly-α-L-glutamic acid-γ-(tert-butyl)ester stage) was no longer detectable by $^1$H-NMR or o-phthalaldehyde analysis.

Example 3E

Poly-α-L-glutamic acid-γ-(tert-butyl)ester (n≈100; 1 g, 0.054 mmol) was dissolved in THF (20 mL) and catalytic DMAP (8 mg, 0.07 mmol) was added. Then 2-thiophenebutyric acid (119 mg, 0.7 mmol) was added to the mixture and immediately after DIPC (160 μL, 1 mmol) was dropwise added. The resulting solution was stirred for about two hours then water (2 volumes) was added and a white precipitate formed immediately. The suspension was stirred for 30 min and filtered, then the white powdered solid was suspended in formic acid (18 mL). The resulting mixture was stirred for 2 h at 60° C. and formic acid was removed by distillation at reduced pressure (P=15 torr) followed by azeotropic distillation with toluene (2×10 mL of toluene) under slight vacuum. The solid residue was dissolved in aqueous NaHCO$_3$ and the resulting solution was filtered on a fiberglass filter (0.2 μm). The filtrate was acidified with H$_2$SO$_4$ 2N until pH 2-2.5. The precipitated material was stirred for 30 min and recovered by filtration yielding, after drying under vacuum (30° C., overnight), the corresponding N-terminus 2-thiophenebutyroyl-capped poly-α-L-glutamic acid, i.e., N-(2-thiophenebutyroyl)-poly-α-L-glutamic acid (480 mg, 76% recovery). The $^1$H-NMR was consistent with the proposed structure.
The N-terminal free amine content (clearly detectable at the poly-α-L-glutamic acid-γ-(tert-butyl)ester stage) was no longer detectable by $^1$H-NMR analysis or by analysis following derivatisation with o-phthalaldehyde.
M$_w$=13,300, polydispersity=1.12 as determined by GPC-MALLS analysis.
According to a very similar procedure, N-(2-thiophenepropanoyl)-poly-α-L-glutamic acid and N-(2-thiophenepentanoyl)-poly-α-L-glutamic acid, were also obtained.
All of the above U.S. patents, U.S. patent application publications, U.S. patent applications, foreign patents, foreign patent applications and non-patent publications referred to in this specification and/or listed in the Application Data Sheet, are incorporated herein by reference, in their entirety.
From the foregoing it will be appreciated that, although specific embodiments of the invention have been described herein for purposes of illustration, various modifications may be made without deviating from the spirit and scope of the invention.

The invention claimed is:
1. A process for the preparation of poly-α-glutamic acid of formula (I)

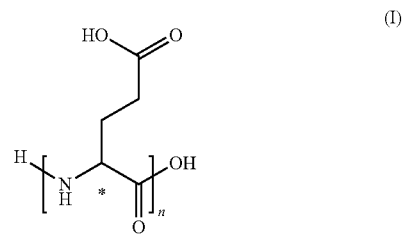

wherein the symbol * indicates a chiral center and n is between 60 and 310, so that the poly-α-glutamic acid has a molecular weight ranging from 8,000 to 40,000 Da said process comprising the steps of:
a) polymerization of a tertiary γ-ester of α-glutamic acid N-carboxy anhydride of formula (II)

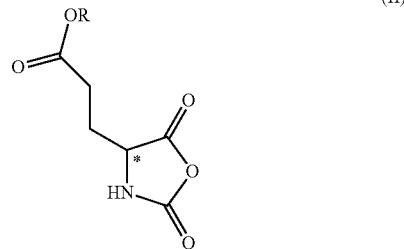

wherein the symbol * is as defined above and R is selected from t-butyl, 1,1-dimethylpropyl and 1,1-dimethylbutyl
in water or in an organic solvent selected from: tetrahydrofuran, 1,4-dioxane, dimethylformamide, 1,4-dioxane/DMF and 1,4-dioxane/tetrahydrofuran mixture with an initiator selected from potassium tert-butoxide, sodium methoxide, diisopropylethylamine, 1,8-diazabicyclo[5,4,0]undec-7-ene, dimethylaminopyridine and L-glutamic acid-γ-tert-butylester, to give a compound of formula (III)

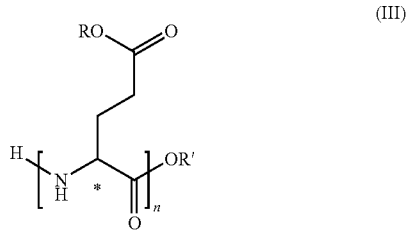

wherein * and R are as defined above and R' is hydrogen when the initiator is selected from diisopropylethylamine, 1,8-diazabicyclo[5,4,0]undec-7-ene, 4-dimethylaminopyridine, glutamic acid dimethyl ester and glutamic acid-γ-tert-butyl ester or R' is a t-butyl or methyl group when the initiator is potassium tert-butoxide and sodium methoxide respectively; and followed by
b) acid hydrolysis of the γ- and α-ester groups to give a compound of formula (I).

2. The process according to claim 1 wherein the solvent is 1,4-dioxane and the initiator is 1,8-diazabicyclo[5,4,0]undec-7-ene.

3. The process according to claim 1 wherein the temperature ranges from 10 to 50° C.

4. The process according to claim 2 wherein the temperature ranges from 10 to 50° C.

5. The process according to claim 1 wherein the concentration of the tertiary γ-ester of α-glutamic acid N-carboxy anhydride ranges from 0.1 to 0.3 M.

6. The process according to claim 2 wherein the concentration of the tertiary γ-ester of α-glutamic acid N-carboxy anhydride ranges from 0.1 to 0.3 M.

7. The process according to claim 3 wherein the concentration of the tertiary γ-ester of α-glutamic acid N-carboxy anhydride ranges from 0.1 to 0.3 M.

8. The process according to claim 4 wherein the concentration of the tertiary γ-ester of α-glutamic acid N-carboxy anhydride ranges from 0.1 to 0.3 M.

9. The process according to claim 1 wherein step b) is carried out in an acid selected from trifluoroacetic acid, formic acid and water/formic acid mixtures at a temperature ranging from 20 to 60° C.

10. The process according to claim 2 wherein step b) is carried out in an acid selected from trifluoroacetic acid, formic acid and water/formic acid mixtures at a temperature ranging from 20 to 60° C.

11. The process according to claim 3 wherein step b) is carried out in an acid selected from trifluoroacetic acid, formic acid and water/formic acid mixtures at a temperature ranging from 20 to 60° C.

12. The process according to claim 4 wherein step b) is carried out in an acid selected from trifluoroacetic acid, formic acid and water/formic acid mixtures at a temperature ranging from 20 to 60° C.

13. The process according to claim 5 wherein step b) is carried out in an acid selected from trifluoroacetic acid, formic acid and water/formic acid mixtures at a temperature ranging from 20 to 60° C.

14. The process according to claim 6 wherein step b) is carried out in an acid selected from trifluoroacetic acid, formic acid and water/formic acid mixtures at a temperature ranging from 20 to 60° C.

15. The process according to claim 7 wherein step b) is carried out in an acid selected from trifluoroacetic acid, formic acid and water/formic acid mixtures at a temperature ranging from 20 to 60° C.

16. The process according to claim 8 wherein step b) is carried out in an acid selected from trifluoroacetic acid, formic acid and water/formic acid mixtures at a temperature ranging from 20 to 60° C.

17. The process according to claim 1 wherein R is t-butyl.

18. The process according to any one of claims 1 to 17 wherein the molecular weight of the poly-α-glutamic acid (I) ranges from 13,000 to 16,000 Da and the polydispersity index is ≦1.5.

19. A process for the preparation of a poly-α-glutamic acid derivative of formula (IV)

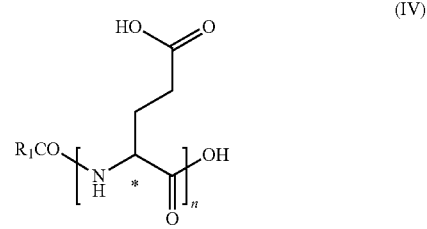

wherein the symbol * indicates a chiral center and n is an integer comprised between 60 and 310 and $R_1CO-$ is selected from:
  $(C_1-C_{10})$alkylcarbonyl;
  $(C_4-C_8)$cycloalkylcarbonyl;
  $(C_2-C_6)$carboxyalkylcarbonyl;
  $(C_6-C_{10})$arylcarbonyl;
  $(C_6-C_{10})$aryl$(C_1-C_{10})$alkylcarbonyl;
  $(C_1-C_{10})$alkyl$(C_6-C_{10})$arylcarbonyl;
  $(C_5-C_{10})$heteroarylcarbonyl and $(C_5-C_{10})$heteroaryl$(C_1-C_{10})$alkylcarbonyl wherein the heteroaromatic ring contains one or more nitrogen, oxygen or sulphur atoms; and
  D- or L-amino acid and non-natural amino acid residues;
said process comprising the steps of:

a) polymerization of a tertiary γ-ester of an α-glutamic acid N-carboxy anhydride of formula (II)

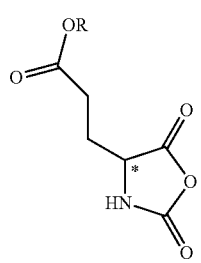
(II)

wherein * is as defined above and R is selected from t-butyl, 1,1-dimethylpropyl and 1,1-dimethylbutyl
in water or in an organic solvent selected from: tetrahydrofuran, 1,4-dioxane, dimethylformamide, 1,4-dioxane/DMF and 1,4-dioxane/tetrahydrofuran mixtures with an initiator selected from potassium tert-butoxide, sodium methoxide, diisopropylethylamine, 1,8-diazabicyclo[5,4,0]undec-7-ene, dimethylaminopyridine, glutamic acid dimethyl ester and L-glutamic acid-γ-tert-butylester, to give a compound of formula (III)

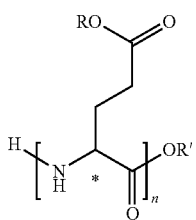
(III)

wherein * n and R are as defined above and R' is hydrogen when the initiator is selected from diisopropylethylamine, 1,8-diazabicyclo[5,4,0]undec-7-ene, 4-dimethylaminopyridine, glutamic acid dimethyl ester and L-glutamic acid-γ-tert-butylester or R' is a t-butyl or methyl group when the initiator is potassium tert-butoxide and sodium methoxide, respectively;

b) reaction of a compound of formula (III) obtained according to step a) above with a carboxylic acid $R_1COOH$, or an acyl chloride $R_1COCl$ or an anhydride $(R_1CO)_2O$ wherein $R_1$ is as defined above, in the presence of a dehydrating agent to give a compound of formula (V)

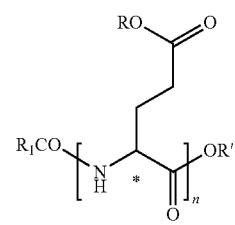
(V)

and
c) the hydrolysis of the compound of formula (V) to give a compound of formula (IV).

20. The process according to claim 19 wherein $(C_{1-10})$ alkylcarbonyl is acetyl or butyryl.

21. The process according to claim 19 wherein $(C_4-C_8)$ cycloalkylcarbonyl is cyclopropylcarbonyl, cyclobutanecarbonyl, or cyclohexylcarbonyl.

22. The process according to claim 19 wherein $(C_2-C_6)$ carboxyalkylcarbonyl is succinyl.

23. The process according to claim 19 wherein $(C_6-C_{10})$ arylcarbonyl is benzoyl, 1-naphthoyl or 2-naphthoyl.

24. The process according to claim 19 wherein $(C_6-C_{10})$ aryl$(C_1-C_{10})$alkylcarbonyl is phenylacetyl or phenylbutyryl.

25. The process according to claim 19 wherein $(C_1-C_{10})$ alkyl$(C_6-C_{10})$aryl carbonyl is o-, m- or p-tolyl.

26. The process according to claim 19 wherein $(C_5-C_{10})$ heteroarylcarbonyl is nicotinoyl, N-methylpyrrole-3-carbonyl, 3-thiophenecarbonyl or 3-quinolinecarbonyl.

27. The process according to claim 19 wherein $(C_5-C_{10})$ heteroaryl$(C_1-C_{10})$alkylcarbonyl is 3-pyridylacetyl.

28. The process according to claim 19 wherein D- or L-natural amino acid residues are those deriving from glycine, alanine, valine, leucine, isoleucine, serine, threonine, lysine, pyroglutamic acid, phenylalanine, tryptophan and cysteine.

29. The process according to claim 28 wherein the amino acid residue is a phenylalanine residue.

30. The process according to claim 19 wherein D or L non-natural amino acid residues are those deriving from β-alanine, α,α-dimethylglycine, α-phenylglycine, homophenylalanine, 3-amino-3-(4-methylphenyl)propionic acid, and 2-(1-aminocyclopentyl)acetic acid.

* * * * *